(12) United States Patent
Galley et al.

(10) Patent No.: US 8,389,507 B2
(45) Date of Patent: Mar. 5, 2013

(54) 2-AZETIDINEMETHANEAMINES AND 2-PYRROLIDINEMETHANEAMINES AS TAAR-LIGANDS

(75) Inventors: Guido Galley, Rheinfelden (DE); Annick Goergler, Colmar (FR); Katrin Groebke Zbinden, Liestal (CH); Roger Norcross, Olsberg (CH); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 165 days.

(21) Appl. No.: 12/176,456

(22) Filed: Jul. 21, 2008

(65) Prior Publication Data

US 2009/0029962 A1  Jan. 29, 2009

(30) Foreign Application Priority Data

Jul. 27, 2007  (EP) .................................... 07113329

(51) Int. Cl.
*A01N 43/00* (2006.01)
*A61K 31/397* (2006.01)

(52) U.S. Cl. .................... 514/210.01; 548/950
(58) Field of Classification Search ............. 514/210.01; 548/950
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,731,471 A | 1/1956 | Synerholm et al. | |
| 2,744,909 A | 5/1956 | Speeter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,354,175 A | 11/1967 | Fruhstorfer et al. | |
| 3,377,247 A | 4/1968 | Elbe | |
| 3,480,630 A | 11/1969 | Stahle et al. | |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,992,403 A | 11/1976 | Roebke | |
| 4,125,620 A | 11/1978 | Stahle et al. | |
| 4,146,647 A | 3/1979 | Lafon | |
| 4,323,570 A | 4/1982 | Stenzel et al. | |
| 4,665,095 A | 5/1987 | Winn et al. | |
| 5,610,174 A | 3/1997 | Craig et al. | |
| 5,658,938 A | 8/1997 | Geerts et al. | |
| 7,652,055 B2 | 1/2010 | Galley et al. | |
| 7,812,047 B2 | 10/2010 | Galley et al. | |
| 7,902,238 B2 | 3/2011 | Galley et al. | |
| 2002/0019390 A1 | 2/2002 | Wong et al. | |
| 2003/0181354 A1 | 9/2003 | Abdulrazik | |
| 2003/0236274 A1 | 12/2003 | Tasaka et al. | |
| 2005/0234101 A1* | 10/2005 | Stenkamp et al. | 514/318 |
| 2007/0066820 A1* | 3/2007 | Sandanayaka et al. | 544/60 |
| 2008/0096906 A1 | 4/2008 | Galley et al. | |

FOREIGN PATENT DOCUMENTS

| | | |
|---|---|---|
| CA | 2246027 | 2/2000 |
| DE | 1695005 | 2/1971 |
| DE | 3133887 | 3/1983 |
| EP | 0 024 829 | 3/1981 |
| EP | 0086043 | 8/1983 |
| EP | 0 125 410 | 11/1984 |
| EP | 0 166 937 | 1/1986 |
| EP | 0 331 374 | 9/1989 |
| EP | 0 424 059 | 4/1991 |
| EP | 0 857 483 | 8/1998 |
| EP | 0 924 209 | 6/1999 |
| EP | 1 103 243 | 5/2001 |
| EP | 1 413 576 | 4/2004 |
| ES | 323 985 | 12/1966 |

(Continued)

OTHER PUBLICATIONS

Nakajima et al. (J. Org. Chem., 1999, 64, 2264-2271.*

(Continued)

*Primary Examiner* — Yong Chu
*Assistant Examiner* — Valerie Rodriguez-Garcia
(74) *Attorney, Agent, or Firm* — George W. Johnston; Patricia S. Rocha-Tramaloni; Kimberly J. Prior

(57) ABSTRACT

The present invention relates to compounds of formula I

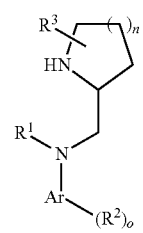

I wherein
$R^1$, $R^2$, $R^3$, Ar, n and o are as defined herein and to their pharmaceutically acceptable active salts. Compounds of formula I have a good affinity to the trace amine associated receptors (TAARs), especially for TAAR1 and are useful for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

4 Claims, No Drawings

FOREIGN PATENT DOCUMENTS

| | | |
|---|---|---|
| FR | 6 551 | 12/1968 |
| GB | 877306 | 9/1961 |
| GB | 1016514 | 1/1966 |
| JP | 2001/089451 | 4/2001 |
| WO | WO 96/22768 | 8/1996 |
| WO | WO 97/12874 | 4/1997 |
| WO | WO 98/12183 | 3/1998 |
| WO | WO 01/30762 | 5/2001 |
| WO | WO 01/81334 | 11/2001 |
| WO | WO 02/18335 | 3/2002 |
| WO | WO 02/22801 | 3/2002 |
| WO | WO 02/40453 | 5/2002 |
| WO | WO 02/76950 | 10/2002 |
| WO | WO 03/092374 | 11/2003 |
| WO | WO 2004/014898 | 2/2004 |
| WO | WO 2006/107923 | 10/2006 |
| WO | WO 2006/119411 | 11/2006 |
| WO | WO 2007/017069 | 2/2007 |
| WO | WO 2007/024944 | 3/2007 |

OTHER PUBLICATIONS

Deutch et al., (1999) Neurotransmitters. In Fundamental Neuroscience (2$^{nd}$ ed.) pp. 193-234, Academic Press.
Wong, et al., (2001) Nat. Rev. Neurosci. 2, pp. 343-351.
Carlsson. et al. (2001) Annu. Rev. Pharmacol. Toxicol. 41, pp. 237-260.
Tuite et al., (2003) Expert Opin. Investig. Drugs 12, pp. 1335-1352.
Castellanos et al., (2002) Nat. Rev. Neurosci. 3, pp. 617-628.
Usdin, E.; Sandler, M.; Editors. Psychopharmacology Series, vol. 1: Trace Amines and the Brain. [Proceedings of a Study Group at the 14th Annual Meeting of the American College of Neuropsychoparmacology, San Juan, Puerto Rico](1976), pp. 1-281.
Lindemann et al., (2005) Trends in Pharmacol. Sci. 26, pp. 274-281.
Branchek et al., (2003) Curr. Opin. Pharmacol. 3, pp. 90-97.
Premont et al. (2001) Proc. Natl. Acad. Sci. U. S. A. 98, pp. 9474-9475.
Mousseau et al., (1995) Prog. Brain Res. 106, pp. 285-291.
McCormack et al. (1986) J. Neurosci. 6, pp. 94-101.
Dyck, L. E. (1989) Life Sci. 44, pp. 1149-1156.
Parker, et al. (1988) J. Pharmacol. Exp. Ther. 245, pp. 199-210.
Lindemann et al. (2005) Genomics 85, pp. 372-385.
Moormann, et al., (1990) J. Med. Chem. pp. 614-626.
Hlasta et al., (1987) vol. 30, J. Med. Chem. pp. 1555-1562.
Dash et al., (2006) J. Heterocyclic Chem. pp. 401-404.
Gentili et al., (2004) J. Med. Chem. vol. 47 pp. 6160-6173.
Dias et al. (2005) J. Med. Chem. vol. 40 pp. 1206-1213.
Pigini et al., (1987) Eur. J. Med. Chem. vol. 22 pp. 273-276.
Wu et al., Synthesis (2003) pp. 1657-1660.
Fujioka et al., (2005) Tetrahedron Lett. vol. 46, pp. 2197-2199.
Ishihara et al., Synlett (2006) pp. 227-230.
Pinza et al. (1976) Heterocycles, vol. 4 pp. 1699-1706.
Kornicka et al. (2006) Heterocycles vol. 68 pp. 687-699.
Kosasayama et al., (1979) Chem. Pharm. Bull. vol. 27 pp. 831-840.
Lloyd et al., (1980) Tetrahedron vol. 36, pp. 2675-2679.
Flippin et al., Tetrahedron Letters, vol. 34, pp. 3255-3258 (1993).
Liebigs, Ann. Chem. pp. 2061-2071 (1980).
Huh et al., Tetrahedron, vol. 58, pp. 9925-9932 (2002).
Huh et al., Tetrahedron, vol. 60, pp. 9857-9862 (2004).
Law et al., J. Med. Chem. vol. 41, pp. 2243-2251 (1998).
Debernardis et al., J. Med. Chem. vol. 29, pp. 1413-1417 (1986).
Mohammadpoor-Baltork, Bull. Korean Chem. Soc. vol. 24, p. 1354-1356 (2003).
Abdollahi-Alibeik et al., Bioorg. Med. Chem. Lett. vol. 14, pp. 6079-6082 (2004).
Amemiya, Synth. Commun. vol. 20, pp. 2483-2489 (1990).
Ohta, Chem. Pharm. Bull. vol. 35, pp. 1058-1069 (1987).
Olah, Synlett pp. 647-650 (1992).
Katz et al., Tetrahedron, vol. 45, pp. 1801-1814 (1989).
Wentland et al., J. Med. Chem. vol. 30, pp. 1482-1489 (1987).
Campos et al., Heterocycles, vol. 40, p. 841-849 (1995).
Ohta, Synthesis, pp. 78-81 (1990).
Mancuso et al., J. Org. Chem. vol. 43, pp. 2480-2482 (1978).
Mohammadpoor-Baltork, Synlett, pp. 2803-2805 (2004).
Cahiez et al., Synthesis, pp. 2138-2144 (1999).
Evans et al., Tetrahedron Lett. vol. 39, pp. 2937-2940 (1998).
Nakamura et al., J. Chem. Soc. Perkin Trans. 1, pp. 1061-1066 (2002).
Turner, et al. (1991) J. Org. Chem. vol. 56, pp. 5739-5740.
Zhang et al., J. Med. Chem. 1997, 40, pp. 3014-3024.
Khimiya Geterotsiklicheskikh Soedinenii, 1988, pp. 77-79.
Reimann et al., Arch. Pharm. 1989, vol. 322, pp. 363-367.
Klapars, et al., J. Am. Chem. Soc. 2001, vol. 123, pp. 7727-7729.
Anderson, et al., Tetrahedron, 2002, vol. 58, pp. 8475-8481.
Touzeau et al., J. Med. Chem. 2003, vol. 46, pp. 1962-1979.
Altenbach et al., Synthesis and Structure-Activity Studies on N-[5-(1H-Imidazol-4-yl)-5,6,7,8-tetrahydro-1-naphthalenyl]methanesulfonamide, an Imidasole-Containing $\alpha_{1A}$-Adrenoceptor Agonist, J. Med. Chem. (2004), 47: 3220-3235.
Amemiya et al., Synthesis and $\alpha$-Adrenergic Activities of 2-and 4-Substituted Imidazoline and Imidazoline Analogues, J. Med. Chem. (1992), 35:750-755.
Bagley et al., Synthesis and $\alpha_2$-Adrenergic Activities of Imidazole and Imidazolidine Analogues: In Vitro and In Vivo Selectivity, Medicinal Chemistry Research (1994), 4:346-364.
Branchek et al., Trace amine receptors as targets for novel therapeutics: legend, myth and fact, Curr. Opin. Phamacol. (2003), 3:90-97.
Bunzow et al., Amphetamine, 3,4-Methylenedioxymethamphetamine, Lysergic Acid Diethylamide, and Metabolites of the catecholamine Neurotransmitters Are Agonists of a Rat Trace Amine Receptor, Molecular Pharmacology (2001), 60: 1181-1188.
Carroll et al., In Vitro and In Vivo Characterization of Alpha-1A Selective Agonists and Their Utility for Stress Incontinence, Med. Chem. Res. (2004), 13:134-148.
De Bernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-1-naphthyl)imidazoline: A Potent Agonist at $\alpha$-Adrenoceptors, J. Med. Chem. (1987), 30:1011-1017.
Faust et al., Antihypertensive Agents: Derivatives of 2-Imidazoline and 1,4,5,6-Tetrahydropyrimidine, J. Org. Chem. (1961), 26: 4044-4047.
Hirashima et al., Three-Dimensional Common-Feature Hypotheses for Octopamine Agonist 2-(Arylimino)imidazolidines, Bioorganic & Medicinal Chemistry (2002), 10:117-123.
Holt, A., Imidazoline binding sites on receptors and enzymes:Emerging targets for novel antidepressant drugs?, Journal of Psychiatry & Neuroscience (2003), 28:409-414.
Jetter et al., Synthesis of 4-Substituted Imidazoles via Palladium-Catalyzed Cross-Coupling Reactions, Synthesis (1998), 829-831.
Law et al., Benzylimidazolines as h5-HT$_{1B/1D}$ Serotonin Receptor Ligands: A Structure-Affinity Investigation, J. Med. Chem. (1998), 41:2243-2251.
Lee et al., 4-[(N-Imidazol-2-ylmethyl)aniline]pyranopyridine Analogs as Novel Anti-Angiogenic Agents, Bull. Korean Chem. Soc. (2005), 25: 619-628.
Matsunaga et al., C$_{17,20}$ inhibitors. Part 2: Design, synthesis and structure-activity relationships of (2-naphthylmethyl)-1H-imidazoles as novel C$_{17,20}$-lyase inhibitors, Bioorganic & Medicinal Chemistry (2004), 4314.
Matsunaga et al., Synthetic studies on (1S)-6,7-dimethoxy-2-naphthyl)-1-(1H-imidazol-4-yl)2-methylpropan-l-ol as a selective C$_{17,20}$-lyase inhibitor, Tetrahedron: Asymmetry (2004), 15: 2021-2028.
McLennan, P;L., The Hypothermic Effect of Clonidine and Other Imidazolidines in Relation to their Ability to Enter the Central Nervous System in Mice, European Journal of Pharmacology (1981), 69:477-482.
Nathanson, J.A.,Phenyliminoimidazolines: Characterization of a Class of Potent Agonists of Octopamine-Sensitive Adenylate Cylcase and Their Use in Understanding the Pharmacology of Octopamine Receptors, Amer. Soc. Pharmacology (1985), 28:254-268.
Ojida et al., Sterocontrolled synthesis of (1S)-1-(1H-imidazol-4-yl)-1-(6-methoxy-2-napthyl)-2-methylpropan-1-ol as a potent C$_{17,20}$-lyase inhibitor,Tetrahedron: Asymmetry (2004), 15: 1555-1559.

Olmos et al., Imidazolines stimulate release of insulin from RIN-5AH cells independently from imidazoline $I_1$ and $I_2$ receptors, European Journal of Pharmacology (1994), 262: 41-48.

Prisinzano et al., 2-(aniline)imidazolines and 2-(benzyl)imidazoline derivatives as $h$5-HT-$_{1D}$ serotonin receptor ligands, Bioorganic & Medicinal Chemistry Letter (2004), 14:4697-4699.

Savola et al., Cardiovascular and Sedative α-Adrenoceptor Effects of Detomidine-like Arylalkyl Imidazoles and Associated Derivatives, Drug Res. (1988), 38:29-35.

Timmermans et al., Characterization of α-Adrenoceptor Populations. Quantitive Relationships between Cardiovascular Effects Initiated at Central and Peripheral α-Adrenoceptors, J. Med. Chem. (1981), 24:502-507.

Timmermans et al., Correlations between Central Hypotensive and Peripheral Hypertensive Effects of Structurally Dissimilar Alpha-Adrenoceptor Agonists, Life Sciences (1981), 28:653-660.

Turner et al., A Facile Route to Imidazol-4-yl Anions and Their Reaction with Carbonyl Compounds, J. Org. Chem. (1991), 56: 5739-5740.

Freiter, E.R., et al., J. Heterocyclic Chem., vol. 10, No. 3, pp. 391-394 (1973), XP008087527.

Tarnchompoo, B., et al., vol. 31, No. 40, pp. 5779-5780 (1990), XP002118267.

Wilkinson, C.F., et al., Biochem. Pharmacol., vol. 21, pp. 3187-3192 (1972), XP :008087536.

Raddatz, Rita , et al., J. Pharmacol. Exp. Therap., vol. 292, No. 3, pp. 1135-1145 (2000), XP008087488.

Shafiee, A., et al., Journal of Heterocyclic Chemistry, pp. 607-610 (1998), XP001069546.

Robertson, David W., J. Med. Chem., vol. 29, pgs. 1577-1586 (1986), XP008087539.

Database CA, Chemical Abstracts, Yamaguchi, Hideaki, XP002465006 & JP 06 268356 (1994).

Nakajima, M. et al *J. of Org. Chem.,* 64(7):2264-2271 (1999).

Huang, K. et al, *Tetrahedron: Asymmetry,* 17:2821-2832 (2006).

(Translation of Jap Off Act in Corres Jap Appl 2010518608 Aug. 21, 2012).

\* cited by examiner

2-AZETIDINEMETHANEAMINES AND 2-PYRROLIDINEMETHANEAMINES AS TAAR-LIGANDS

PRIORITY TO RELATED APPLICATION(S)

This application claims the benefit of European Patent Application No. 07113329.2, filed Jul. 27, 2007, which is hereby incorporated by reference in its entirety.

BACKGROUND OF THE INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

REFERENCES USED

1. Deutch, A. Y. and Roth, R. H. (1999) Neurotransmitters. In *Fundamental Neuroscience* (2$^{nd}$ edn) (Zigmond, M. J., Bloom, F. E., Landis, S. C., Roberts, J. L, and Squire, L. R., eds.), pp. 193-234, Academic Press;
2. Wong, M. L. and Licinio, J. (2001) Research and treatment approaches to depression. *Nat. Rev. Neurosci.* 2, 343-351;
3. Carlsson, A. et al. (2001) Interactions between monoamines, glutamate, and GABA in schizophrenia: new evidence. *Annu. Rev. Pharmacol. Toxicol.* 41, 237-260;
4. Tuite, P. and Riss, J. (2003) Recent developments in the pharmacological treatment of Parkinson's disease. *Expert Opin. Investig. Drugs* 12, 1335-1352,
5. Castellanos, F. X. and Tannock, R. (2002) Neuroscience of attention-deficit/hyperactivity disorder: the search for endophenotypes. *Nat. Rev. Neurosci.* 3, 617-628;
6. Usdin, Earl; Sandler, Merton; Editors. *Psychopharmacology Series, Vol.* 1: *Trace Amines and the Brain. [Proceedings of a Study Group at the* 14th *Annual Meeting of the American College of Neuropsychoparmacology*, San Juan, Puerto Rico] (1976);
7. Lindemann, L. and Hoener, M. (2005) A renaissance in trace amines inspired by a novel GPCR family. *Trends in Pharmacol. Sci.* 26, 274-281;
8. Branchek, T. A. and Blackburn, T. P. (2003) Trace amine receptors as targets for novel therapeutics: legend, myth and fact. *Curr. Opin. Pharmacol.* 3, 90-97;
9. Premont, R. T. et al. (2001) Following the trace of elusive amines. *Proc. Natl. Acad. Sci. U.S.A.* 98, 9474-9475;
10. Mousseau, D. D. and Butterworth, R. F. (1995) A high-affinity [3H] tryptamine binding site in human brain, *Prog. Brain Res.* 106, 285-291;
11. McCormack, J. K. et al. (1986) Autoradiographic localization of tryptamine binding sites in the rat and dog central nervous system. *J. Neurosci.* 6, 94-101;
12. Dyck, L. E. (1989) Release of some endogenous trace amines from rat striatal slices in the presence and absence of a monoamine oxidase inhibitor. *Life Sci.* 44, 1149-1156;
13. Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;
14. Lindemann, L. et al. (2005) Trace amine associated receptors form structurally and functionally distinct subfamilies of novel G protein-coupled receptors. *Genomics* 85, 372-385.

SUMMARY OF THE INVENTION

The present invention provides compounds of formula I

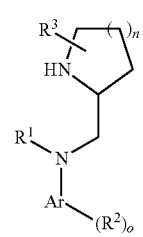

wherein
R$^1$ is hydrogen, lower alkyl or benzyl which is optionally substituted by halogen or lower alkoxy;
R$^2$ is hydrogen, halogen or OR, wherein R is lower alkyl, aryl or lower alkyl substituted by halogen;
R$^3$ is hydrogen or fluorine;
Ar is phenyl;

n is 0 or 1; and
o is 0, 1 or 2;
and to their pharmaceutically active salts.

The invention includes all racemic mixtures, all their corresponding enantiomers and/or optical isomers.

The invention also provides pharmaceutical compositions containing a therapeutically effective amount of a compound of formula I and a pharmaceutically acceptable carrier. The invention further provides methods for the manufacture of the compounds and compositions of the invention.

Compounds of formula I have a good affinity to the trace amine associated receptors (TAARs), especially for TAAR1.

The compounds are useful for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety and attention deficit hyperactivity disorder (ADHD).

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes the group OR where R is lower alkyl as defined above.

As used herein, the term "lower alkyl substituted by halogen" denotes a lower alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

As used herein, the term "aryl" denotes an aromatic group, selected from phenyl or naphthalen-1-yl.

The term "halogen" denotes chlorine, iodine, fluorine and bromine.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

Preferred compounds of formula I are those, wherein n is 1 (pyrrolidine):

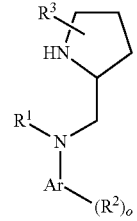

IA wherein
$R^1$ is hydrogen, lower alkyl or benzyl which is optionally substituted by halogen or lower alkoxy;
$R^2$ is hydrogen, halogen or OR, wherein R is lower alkyl, aryl or lower alkyl substituted by halogen;
$R^3$ is hydrogen or fluorine;
Ar is phenyl; and
o is 0, 1 or 2;
and their pharmaceutically active salts.

Examples of compounds of formula IA are
ethyl-(3-phenoxy-phenyl)-(R)-1-pyrrolidin-2-ylmethyl-amine,
ethyl-(3-phenoxy-phenyl)-(S)-1-pyrrolidin-2-ylmethyl-amine,
(3,4-dichloro-phenyl)-ethyl-(S)-1-pyrrolidin-2-ylmethyl-amine,
(4-chloro-3-methoxy-phenyl)-methyl-(S)-1-pyrrolidin-2-ylmethyl-amine,
(4-chloro-3-methoxy-phenyl)-ethyl-(S)-1-pyrrolidin-2-ylmethyl-amine,
(4-chloro-phenyl)-ethyl-(S)-1-pyrrolidin-2-ylmethyl-amine,
(4-chloro-3-methoxy-phenyl)-isopropyl-(S)-1-pyrrolidin-2-ylmethyl-amine,
(3,4-dichloro-phenyl)-isopropyl-(S)-1-pyrrolidin-2-ylmethyl-amine, and
(4-chloro-phenyl)-ethyl-(R)-1-pyrrolidin-2-ylmethyl-amine.

Preferred compounds are further those, wherein n is 0 (azetidine):

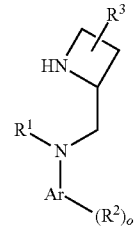

IB wherein
$R^1$ is hydrogen, lower alkyl or benzyl which is optionally substituted by halogen or lower alkoxy;
$R^2$ is hydrogen, halogen or OR, wherein R is lower alkyl, aryl or lower alkyl substituted by halogen;
$R^3$ is hydrogen or fluorine;
Ar is phenyl; and
o is 0, 1 or 2;
and their pharmaceutically active salts.

Examples of compounds of formula IB are
(S)-1-azetidin-2-ylmethyl-(4-chloro-phenyl)-ethyl-amine,
(S)-1-azetidin-2-ylmethyl-ethyl-phenyl-amine, (S)-1-azetidin-2-ylmethyl-ethyl-(3-methoxy-phenyl)-amine,
(S)-1-azetidin-2-ylmethyl-(3-bromo-phenyl)-ethyl-amine,
(S)-1-azetidin-2-ylmethyl-(4-chloro-phenyl)-methyl-amine,
(S)-1-azetidin-2-ylmethyl-(4-chloro-phenyl)-isopropyl-amine,
(S)-1-azetidin-2-ylmethyl-benzyl-(4-chloro-phenyl)-amine.

The present compounds of formula I and their pharmaceutically acceptable salts can be prepared by methods known in the art, for example, by processes described below, a) reacting a compound of formula

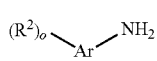

II with a compound of formula

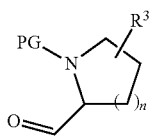

III to give a compound of formula

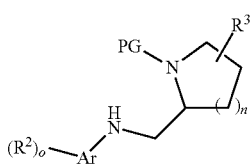

IV and deprotecting a compound of formula IV to give a compound of formula

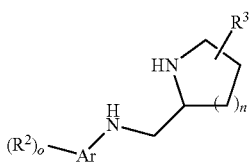

I-1 wherein the substituents are as defined above, or b) reacting a compound of formula

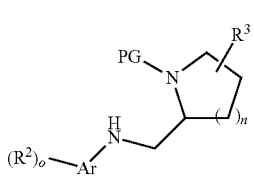

IV with an aldehyde of formula $R^{1'}$—CHO to give a compound of formula

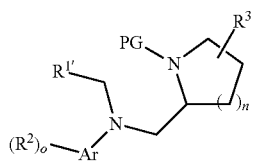

IV-1 and deprotecting a compound of formula IV-I to a compound of formula

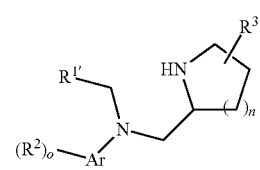

I-2 wherein $R^{1'}$ is lower alkyl or hydrogen and the other definitions are as described above, or c) reacting a compound of formula

II-1 with a compound of formula

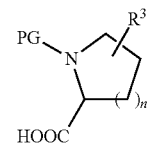

VIII to give a compound of formula

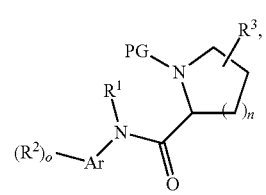

IX reducing the compound of formula IX and deprotecting to a compound of formula

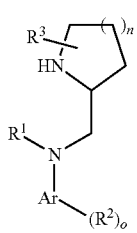

wherein the substituents are as defined above, and, if desired, converting the compounds obtained into pharmaceutically acceptable acid addition salts.

The compounds of formula I can be prepared in accordance with the process variants as described above and with the following schemes 1-3. The starting materials are either commercially available, are otherwise known in the chemical literature, or can be prepared in accordance with methods well known in the art.

Method 1

Scheme 1

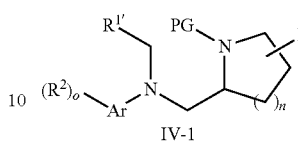

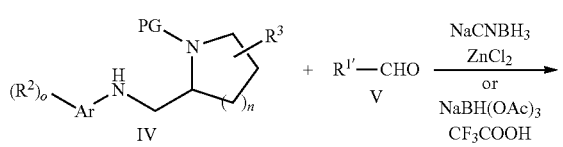

Compounds of formula I-1 can be prepared by reductive amination using an aniline of formula II and an N-protected pyrrolidine-2-carbaldehyde of formula III (n=1) or an N-protected 2-formylazetidine of formula III (n=0) in the presence of an reducing agent such as NaCNBH$_3$ or NaBH(OAc)$_3$ followed by a deprotection step on the intermediate IV in the usual matter.

Method 2

Scheme 2

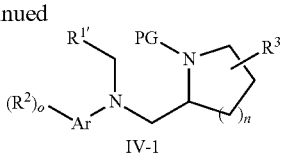

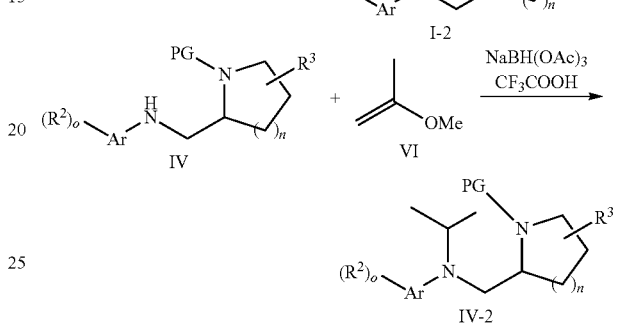

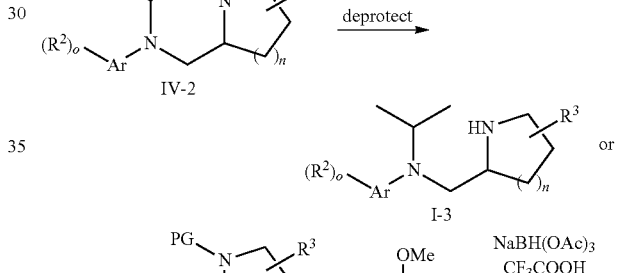

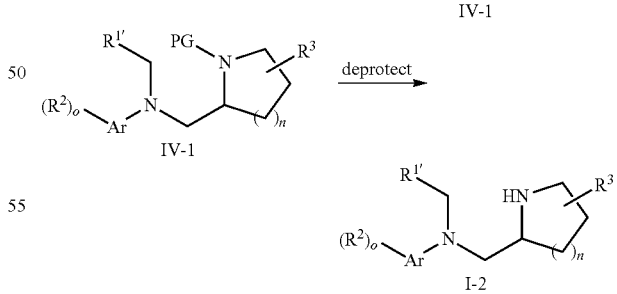

Compounds of formula I-2 and I-3 can be prepared by a second reductive amination step starting from intermediate IV using for instance reagents such as an aldehyde V, an enolether VI or an aldehyde acetal VII in presence of an reducing agent such as NaCNBH$_3$ or NaBH(OAc)$_3$ followed by N-deprotection of the pyrrolidine or azetidine in the usual matter.

Method 3

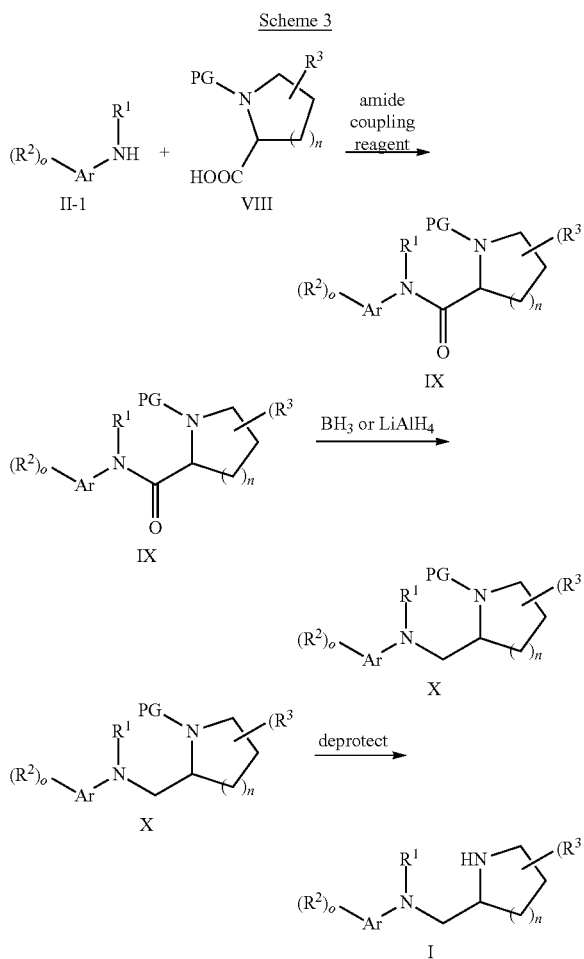

Scheme 3 describes the preparation of a compound of formula I by formation of an amide IX followed by reduction of the amide bond by a reducing agent such as borane or lithium aluminumhydride and protecting group removal in the usual matter.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR1 were amplified from genomic DNA essentially as described by Lindemann et al. [14]. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC #CRL-1573) were cultured essentially as described Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. Cell pellet was then suspended in 20 ml HEPES-NaOH (20 mM), pH 7.4 containing 10 mM EDTA, and homogenized with a Polytron (PT 3000, Kinematica) at 10,000 rpm for 10 s. The homogenate was centrifuged at 48,000×g for 30 min at 4° C. and the pellet resuspended in 20 ml HEPES-NaOH (20 mM), pH 7.4 containing 0.1 mM EDTA (buffer A), and homogenized with a Polytron at 10,000 rpm for 10 s. The homogenate was then centrifuged at 48,000×g for 30 min at 4° C. and the pellet resuspended in 20 ml buffer A, and homogenized with a Polytron at 10,000 rpm for 10 s. Protein concentration was determined by the method of Pierce (Rockford, Ill.). The homogenate was then centrifuged at 48,000×g for 10 min at 4° C., resuspended in HEPES-NaOH (20 mM), pH 7.0 including $MgCl_2$ (10 mM) and $CaCl_2$ g protein per ml and (2 mM) (buffer B) at 200 homogenized with a Polytron at 10,000 rpm for 10 s.

Binding assay was performed at 4° C. in a final volume of 1 ml, and with an incubation time of 30 min. The radioligand [$^3$H]-rac-2-(1,2,3,4-tetrahydro-1-naphthyl)-2-imidazoline was used at a concentration equal to the calculated $K_d$ value of 60 nM to give a bound at around 0.1% of the total added radioligand concentration, and a specific binding which represented approximately 70-80% of the total binding. Non-specific binding was defined as the amount of [$^3$H]-rac-2-(1, 2,3,4-tetrahydro-1-naphthyl)-2-imidazoline bound in the presence of the appropriate unlabelled ligand (10 μM). Competing ligands were tested in a wide range of concentrations (10 μM-30 μM). The final dimethylsulphoxide concentration in the assay was 2%, and it did not affect radioligand binding. Each experiment was performed in duplicate. All incubations were terminated by rapid filtration through UniFilter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 μl/well, Packard Instrument Company) and bound radioactivity was counted by a TopCount Microplate Scintillation Counter (Packard Instrument Company).

The preferred compounds show a Ki value (μM) in mouse on TAAR1 in the range of <0.1 μM. Representative compounds are shown in the table below.

| Example | Ki (μM) mouse | Example | Ki (μM) mouse | Example | Ki |
|---|---|---|---|---|---|
| 3 | 0.0044 | 12 | 0.0213 | 19 | 0.0137 |
| 4 | 0.0172 | 13 | 0.005 | 20 | 0.0047 |
| 6 | 0.0028 | 16 | 0.0056 | 21 | 0.021 |
| 8 | 0.0859 | 17 | 00024 | 22 | 0.041 |
| 9 | 0.0092 | 18 | 0.0092 | 23 | 0.0107 |
| 11 | 0.0131 | | | | |

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, depression, cognitive impairment and Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | mg/tablet | | | |
| Item Ingredients | 5 mg | 25 mg | 100 mg | 500 mg |
| 1. Compound of formula I | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | mg/capsule | | | |
| Item Ingredients | 5 mg | 25 mg | 100 mg | 500 mg |
| 1. Compound of formula I | 5 | 25 | 100 | 500 |
| 2. Hydrous Lactose | 159 | 123 | 148 | — |
| 3. Corn Starch | 25 | 35 | 40 | 70 |

| | | | | |
|---|---|---|---|---|
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXPERIMENTAL

The following examples illustrate the invention but are not intended to limit its scope.

Example 1

(3-Phenoxy-phenyl)-(R)-1-pyrrolidin-2-ylmethyl-amine

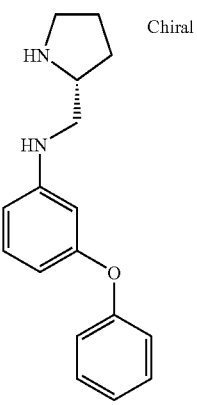 [SMILES: c1ccc(Oc2cccc(NC[C@H]3CCCN3)c2)cc1]

To a solution of 3-phenoxyaniline (0.3 g, 1.62 mmol) in 1,2-dichloroethane (4 ml) were added N-(tert-butoxycarbonyl)-D-prolinal (0.322 g, 1.62 mmol) and sodium triacetoxyborohydride (0.480 g, 2.26 mmol). The resulting suspension was stirred overnight at 50° C. The mixture was then cooled to room temperature, water (8 ml) was added and extracted with ethyl acetate (3×20 ml). The combined organic layers were dried with magnesium sulphate, filtered and concentrated in vacuo. The residue was purified by flash chromatography (SiO$_2$: heptane/ethyl acetate=70:30) to yield a light yellow oil that was dissolved in dichloromethane (4 ml). Trifluoroacetic acid (1 ml) was added and the mixture was stirred for 3 h at room temperature. Aqueous sodium hydroxide solution (4N) was added until basic pH and the mixture was extracted with ethyl acetate (2 times 30 ml). The combined organic layers were dried with magnesium sulphate, filtered and concentrated in vacuo. The residue was purified by flash chromatography (column: Isolute® Flash-NH$_2$ from Separtis; eluent: ethyl acetate) to yield a colourless oil, (0.256 g, 59%); MS (ISP): 269.1 ((M+H)$^+$).

Example 2

(3-Phenoxy-phenyl)-(S)-1-pyrrolidin-2-ylmethyl-amine

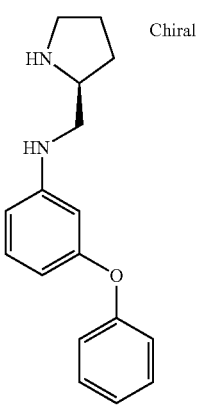 [SMILES: c1ccc(Oc2cccc(NC[C@@H]3CCCN3)c2)cc1]

The title compound, MS (ISP): 269.1 ([M+H]$^+$) was obtained in comparable yield analogous to the procedure described for Example 1 using N-(tert-butoxycarbonyl)-L-prolinal instead of N-(tert-butoxycarbonyl)-D-prolinal.

Example 3

Ethyl-(3-phenoxy-phenyl)-(R)-1-pyrrolidin-2-ylm-ethyl-amine

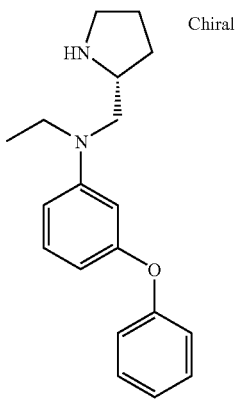 [SMILES: CCN(C[C@H]1CCCN1)c1cccc(Oc2ccccc2)c1]

a) (R)-2-{[Ethyl-(3-phenoxy-phenyl)-amino]-methyl}-pyrrolidine-1-carboxylic acid tert-butyl ester To a solution of 3-phenoxyaniline (0.3 g, 1.62 mmol) in 1,2-dichloroethane (4 ml) were added N-(tert-butoxycarbonyl)-D-prolinal (0.322 g, 1.62 mmol) and sodium triacetoxyborohydride (0.480 g, 2.26 mmol). The resulting suspension was stirred overnight at 50° C. The mixture was then cooled to room temperature, water (8 ml) was added and extracted with ethyl acetate (3×20 ml). The combined organic layers were dried with magnesium sulphate, filtered and concentrated in vacuo. The residue was purified by flash chromatography (SiO$_2$: heptane/ethyl acetate=70:30) to yield a light yellow oil that was dissolved in methanol (8 ml). Acetaldehyde (0.134 g, 3.05 mmol), zinc chloride (0.333 g, 2.44 mmol) and sodium cyanoborohydride (0.115 g, 1.83 mmol) were added and the mixture was stirred overnight at 40° C. Saturated ammonium acetate solution (10 ml) was added and extracted with ethyl acetate (3×30 ml). The combined organic layers were dried with magnesium sulphate, filtered and concentrated in vacuo. The residue was purified by flash chromatography (SiO$_2$: heptane/ethyl acetate=70:30) to yield 0.43 g (67%) of a colourless oil; MS (ISP): 397.0 ((M+H)$^+$).

b) Ethyl-(3-phenoxy-phenyl)-(R)-1-pyrrolidin-2-ylmethyl-amine

To a solution of (R)-2-{[ethyl-(3-phenoxy-phenyl)-amino]-methyl}-pyrrolidine-1-carboxylic acid tert-butyl ester (0.162 g, 0.41 mmol) in dichloromethane (3 ml) was added trifluoroacetic acid (1 ml) and the mixture was stirred for 3 h at room temperature. Aqueous sodium hydroxide solution (4N) was added until basic pH and the mixture was extracted with ethyl acetate (2 times 30 ml). The combined organic layers were dried with magnesium sulphate, filtered and concentrated in vacuo. The residue was purified by flash chromatography (column: Isolute® Flash-NH$_2$ from Separtis; eluent: ethyl acetate) to yield a colourless oil, (0.043 g, 36%); MS (ISP): 297.5 ((M+H)$^+$).

Example 4

Ethyl-(3-phenoxy-phenyl)-(S)-1-pyrrolidin-2-ylm-ethyl-amine

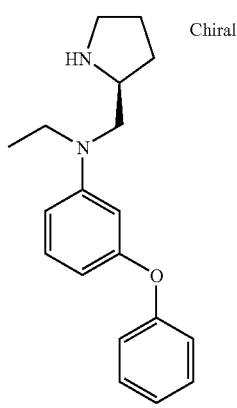 [SMILES: CCN(C[C@@H]1CCCN1)c1cccc(Oc2ccccc2)c1]

The title compound, MS (ISP): 297.5 ([M+H]$^+$) was obtained in comparable yield analogous to the procedure described for Example 3 using N-(tert-butoxycarbonyl)-L-prolinal instead of N-(tert-butoxycarbonyl)-D-prolinal in step a).

Example 5

(3-Bromo-phenyl)-ethyl-(S)-1-pyrrolidin-2-ylm-ethyl-amine

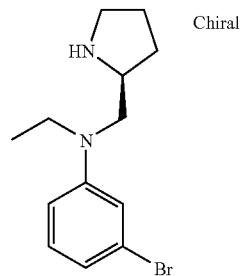 [SMILES: CCN(C[C@@H]1CCCN1)c1cccc(Br)c1]

The title compound, MS (ISP): 283.1; 285.1 ([M+H]$^+$) was obtained in comparable yield analogous to the procedure described for Example 3 using N-(tert-butoxycarbonyl)-L-prolinal instead of N-(tert-butoxycarbonyl)-D-prolinal and 3-bromoaniline instead of 3-phenoxyaniline in step a).

Example 6

(3,4-Dichloro-phenyl)-ethyl-(S)-1-pyrrolidin-2-ylm-ethyl-amine

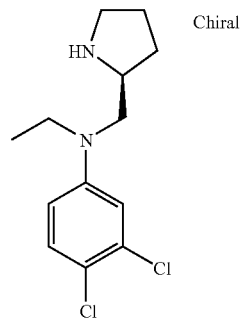 [SMILES: CCN(C[C@@H]1CCCN1)c1ccc(Cl)c(Cl)c1]

The title compound, MS (ISP): 273.2; 275.1 ([M+H]$^+$) was obtained in comparable yield analogous to the procedure described for Example 3 using N-(tert-butoxycarbonyl)-L- prolinal instead of N-(tert-butoxycarbonyl)-D-prolinal and 3,4-dichloroaniline instead of 3-phenoxyaniline in step a).

Example 7

Ethyl-(S)-1-pyrrolidin-2-ylmethyl-(3-trifluoromethoxy-phenyl)-amine

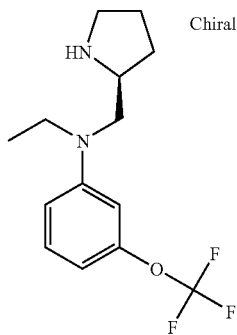 [SMILES: CCN(C[C@@H]1CCCN1)c1cccc(OC(F)(F)F)c1]

The title compound, MS (ISP): 289.0 ([M+H]$^{+\cdot}$) was obtained in comparable yield analogous to the procedure described for Example 3 using N-(tert-butoxycarbonyl)-L-prolinal instead of N-(tert-butoxycarbonyl)-D-prolinal and 3-trifluoromethoxy-aniline instead of 3-phenoxyaniline in step a).

Example 8

(4-Chloro-3-methoxy-phenyl)-methyl-(S)-1-pyrrolidin-2-ylmethyl-amine

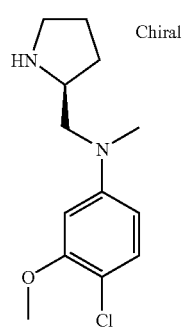 [SMILES: COc1cc(N(C)C[C@@H]2CCCN2)ccc1Cl]

The title compound, MS (ISP): 255.3 ([M+H]$^{+\cdot}$) was obtained in comparable yield analogous to the procedure described for Example 3 using N-(tert-butoxycarbonyl)-L-prolinal instead of N-(tert-butoxycarbonyl)-D-prolinal, 4-chloro-3-methoxy-aniline instead of 3-phenoxyaniline and paraformaldehyde instead of acetaldehyde in step a).

Example 9

(4-Chloro-3-methoxy-phenyl)-ethyl-(S)-1-pyrrolidin-2-ylmethyl-amine

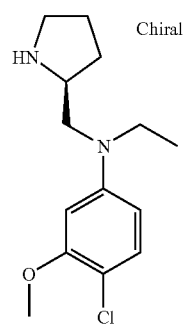

The title compound, MS (ISP): 269.4 ([M+H]$^{+\cdot}$) was obtained in comparable yield analogous to the procedure described for Example 3 using N-(tert-butoxycarbonyl)-L-prolinal instead of N-(tert-butoxycarbonyl)-D-prolinal and 4-chloro-3-methoxy-aniline instead of 3-phenoxyaniline in step a).

Example 10

(4-Chloro-phenyl)-methyl-(S)-1-pyrrolidin-2-ylmethyl-amine

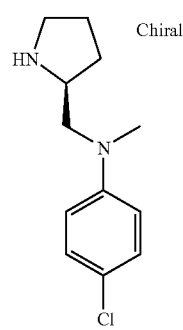

The title compound, MS (ISP): 225.3 ([M+H]$^{+\cdot}$) was obtained in comparable yield analogous to the procedure described for Example 3 using N-(tert-butoxycarbonyl)-L-prolinal instead of N-(tert-butoxycarbonyl)-D-prolinal, 4-chloroaniline instead of 3-phenoxyaniline and paraformaldehyde instead of acetaldehyde in step a).

Example 11

(4-Chloro-phenyl)-ethyl-(S)-1-pyrrolidin-2-ylmethyl-amine

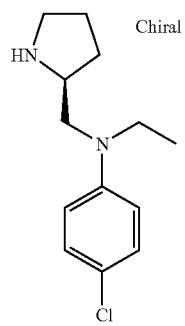 [SMILES: CCN(C[C@@H]1CCCN1)c1ccc(Cl)cc1]

The title compound, MS (ISP): 239.3 ([M+H]$^{+\cdot}$) was obtained in comparable yield analogous to the procedure described for Example 3 using N-(tert-butoxycarbonyl)-L-prolinal instead of N-(tert-butoxycarbonyl)-D-prolinal and 4-chloroaniline instead of 3-phenoxyaniline in step a).

Example 12

(4-Chloro-3-methoxy-phenyl)-isopropyl-(S)-1-pyrrolidin-2-ylmethyl-amine

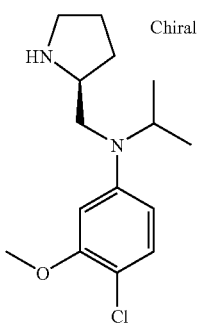 [SMILES: COc1cc(N(C[C@@H]2CCCN2)C(C)C)ccc1Cl]

a) (S)-2-[(4-Chloro-3-methoxy-phenylamino)-methyl]-pyrrolidine-1-carboxylic acid tert-butyl ester To a solution of 4-chloro-3-methoxyaniline (1.57 g, 10.0 mmol) in methanol (27 ml) were added acetic acid (3 ml), N-(tert-butoxycarbonyl)-L-prolinal (2.40 g, 12.05 mmol) and sodium cyanoborohydride (1.56 g, 24.1 mmol). The resulting suspension was stirred for 2 hours at room temperature. Aqueous sodium bicarbonate solution (30 ml) was added and the mixture was extracted with ethyl acetate (3×20 ml). The combined organic layers were dried with magnesium sulphate, filtered and concentrated in vacuo. The residue was purified by flash chromatography (SiO2: heptane/ethyl acetate=70:30) to yield a light yellow oil (2.31 g, 68%); MS (ISP): 341.0, 342.9 ((M+H)$^{+\cdot}$).

b) (4-Chloro-3-methoxy-phenyl)-isopropyl-(S)-1-pyrrolidin-2-ylmethyl-amine

To a solution of (S)-2-[(4-chloro-3-methoxy-phenylamino)-methyl]-pyrrolidine-1-carboxylic acid tert-butyl ester (0.68 g, 2.0 mmol) were added 2-methoxypropene (0.216 g, 3.0 mmol), trifluoracetic acid (0.228 g, 2.0 mmol) and sodium triacetoxyborohydride (0.64 g, 3.0 mmol). The mixture was stirred overnight at 60° C. Saturated sodium bicarbonate solution (10 ml) was added and the mixture was extracted with ethyl acetate (3×30 ml). The combined organic layers were dried with magnesium sulphate, filtered and concentrated in vacuo. The residue was dissolved in dichloromethane (3 ml) and trifluoroacetic acid (3 ml) was added. Solvent and access trifluoroacetic acid was evaporated, diisopropylethylamine (1 ml) was added to liberate the free base and the mixture was purified by flash chromatography (column: Isolute® Flash-NH$_2$ from Separtis; eluent: ethyl acetate/heptane 1:1) to yield a light yellow oil, (0.185 g, 33%); MS (ISP): 283.5, 285.2 ((M+H)$^{+\cdot}$).

Example 13

(3,4-Dichloro-phenyl)-isopropyl-(S)-1-pyrrolidin-2-ylmethyl-amine

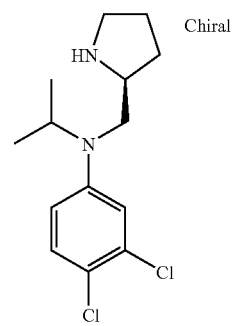 [SMILES: CC(C)N(C[C@@H]1CCCN1)c1ccc(Cl)c(Cl)c1]

The title compound, MS (ISP): 287.1, 289.1 ([M+H]$^{+\cdot}$) was obtained in comparable yield analogous to the procedure described for Example 12 using 3,4-dichloroaniline instead of 4-chloro-3-methoxyaniline in step a).

Example 14

Benzyl-(3,4-dichloro-phenyl)-(S)-1-pyrrolidin-2-ylmethyl-amine

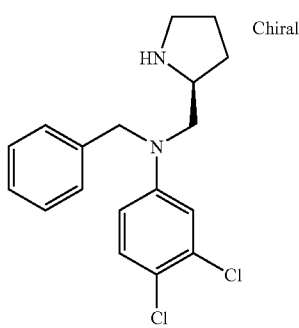 [SMILES: Clc1ccc(N(Cc2ccccc2)C[C@@H]2CCCN2)cc1Cl]

The title compound, MS (ISP): 335.3, 337.2 ([M+H]+·) was obtained in comparable yield analogous to the procedure described for Example 12 using 3,4-dichloroaniline instead of 4-chloro-3-methoxyaniline in step a) and benzaldehyde dimethylacetal instead of 2-methoxypropene in step b).

Example 15

(4-Chloro-phenyl)-ethyl-((2S,4S)-4-fluoro-pyrrolidin-2-ylmethyl)-amine

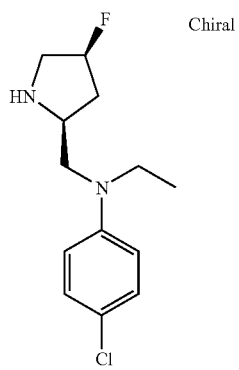 [SMILES: CCN(C[C@@H]1C[C@H](F)CN1)c1ccc(Cl)cc1]

To a solution of N-ethyl-4-chloro-aniline (0.31 g, 2.0 mmol) in dichloromethane (8 ml) were added (2S,4S)-tert-butyloxycarbonyl-4-fluoro-pyrrolidine-2-carboxylic acid (0.47 g, 2.0 mmol), bis(2-oxo-3-oxazolidinyl)-phosphinic chloride (0.76 g, 3.0 mmol) and diisopropylethylamine (0.39 g, 3.0 mmol). The mixture was stirred for 3 days at room temperature. Aqueous sodium bicarbonate solution (20 ml) was added and the mixture was extracted with dichloromethane (3×20 ml). The combined organic layers were dried with magnesium sulphate, filtered and concentrated in vacuo. The residue was purified by flash chromatography (SiO2: heptane/ethyl acetate=2:1) to yield a light yellow oil (0.55 g), that was dissolved in tetrahydrofurane (15 ml). Borane-tetrahydrofurane-complex (7.4 ml, 1M, 7.4 mmol) was added and the mixture was heated at 60° C. overnight. After cooling 5 drops of aqueous hydrochloric acid (4N) were added and the solvent was evaporated. The white residue was dissolved in aqueous hydrochloric acid (4N, 10 ml) and heated at 60° C. for 1 hour. After cooling aqueous sodium hydroxide solution was added until basic pH and the mixture was extracted with dichloromethane (2×30 ml). The combined organic layers were dried with magnesium sulphate, filtered and concentrated in vacuo. The residue was purified by flash chromatography (column: Isolute® Flash-NH2 from Separtis; eluent: ethyl acetate/heptane 1:1) to yield a light yellow oil, (0.137 g, 27%); MS (ISP): 257.1 ((M+H)+·).

Example 16

(4-Chloro-phenyl)-ethyl-(R)-1-pyrrolidin-2-ylmethyl-amine

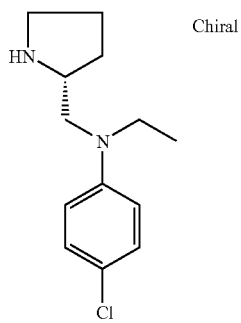 [SMILES: CCN(C[C@H]1CCCN1)c1ccc(Cl)cc1]

The title compound, MS (ISP): 239.0, 241.1 ([M+H]+·) was obtained in comparable yield analogous to the procedure described for Example 3 using 4-chloroaniline instead of 3-phenoxyaniline in step a).

Example 17

(S)-1-Azetidin-2-ylmethyl-(4-chloro-phenyl)-ethyl-amine

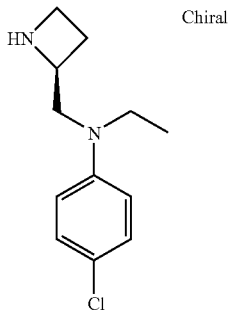

a) (S)-2-[(4-Chloro-phenylamino)-methyl]-azetidine-1-carboxylic acid tert-butyl ester To a solution of 4-chloro-aniline (0.57 g, 4.5 mmol) in methanol (18 ml) were added acetic acid (2 ml), (S)-2-formyl-azetidine-1-carboxylic acid tert.butyl ester (1.74 g, 9.4 mmol) and after 15 min stirring sodium cyanoborohydride (0.57 g, 9.0 mmol). The resulting suspension was stirred for 2 hours at room temperature. Aqueous sodium bicarbonate solution (20 ml) was added and the mixture was extracted with ethyl acetate (3×20 ml). The combined organic layers were dried with magnesium sulphate, filtered and concentrated in vacuo. The residue was purified by flash chromatography (SiO2: heptane/ethyl acetate=9:1) to yield a colourless oil (0.99 g, 74%); MS (ISP): 297.1 ((M+H)+·); 241.3 ((M−C(CH3)3+H)+·).

b) (S)-1-Azetidin-2-ylmethyl-(4-chloro-phenyl)-ethyl-amine (S)-2-[(4-Chloro-phenylamino)-methyl]-azetidine-1-carboxylic acid tert-butyl ester (0.08 g, 0.27 mmol) was dissolved in methanol (3 ml), then acetaldehyde (0.059 g, 1.35 mmol), zinc chloride (0.147 g, 1.1 mmol) and sodium cyanoborohydride (0.51 g, 0.81 mmol) were added and the mixture was stirred overnight at 40° C. Saturated ammonium acetate solution (10 ml) was added and extracted with ethyl acetate (3×30 ml). The combined organic layers were dried with magnesium sulphate, filtered and concentrated in vacuo. The residue was dissolved in dichloromethane (3 ml) and trifluoroacetic acid (3 ml) was added. Solvent and access trifluoroacetic acid was evaporated, diisopropylethylamine (0.3 ml) was added to liberate the free base and the mixture was purified by flash chromatography (column: Isolute® Flash-NH$_2$ from Separtis; eluent: ethyl acetate/heptane 1:1) to yield a light yellow gum, (0.022 g, 38%); MS (ISP): 225.1 ((M+H)$^+$).

Example 18

(S)-1-Azetidin-2-ylmethyl-ethyl-phenyl-amine

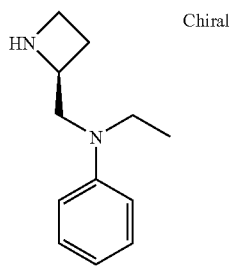

The title compound, MS (ISP): 191.4 ([M+H]$^+$) was obtained in comparable yield analogous to the procedure described for Example 17 using aniline instead of 4-chloroaniline in step a).

Example 19

(S)-1-Azetidin-2-ylmethyl-ethyl-(3-methoxy-phenyl)-amine

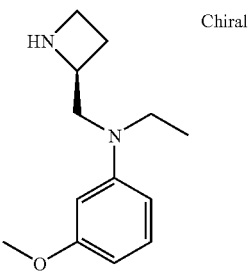 [SMILES: CCN(C[C@@H]1CCN1)c1cccc(OC)c1]

The title compound, MS (ISP): 221.4 ([M+H]$^+$) was obtained in comparable yield analogous to the procedure described for Example 17 using 3-methoxyaniline instead of 4-chloroaniline in step a).

Example 20

(S)-1-Azetidin-2-ylmethyl-(3-bromo-phenyl)-ethyl-amine

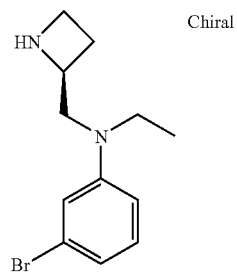

The title compound, MS (ISP): 269.4; 271.4 ([M+H]$^+$) was obtained in comparable yield analogous to the procedure described for Example 17 using 3-bromoaniline instead of 4-chloroaniline in step a).

Example 21

(S)-1-Azetidin-2-ylmethyl-(4-chloro-phenyl)-methyl-amine

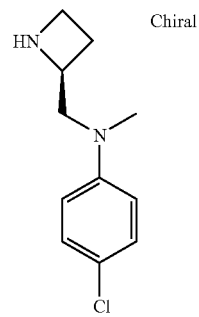

The title compound, MS (ISP): 211.1 ([M+H]$^+$) was obtained in comparable yield analogous to the procedure described for Example 17 using paraformaldehyde instead of acetaldehyde in step b).

Example 22

(S)-1-Azetidin-2-ylmethyl-(4-chloro-phenyl)-isopropyl-amine

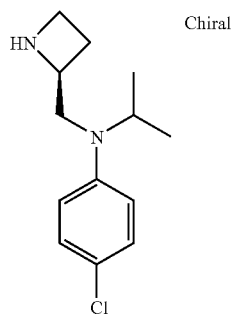 [SMILES: CC(C)N(C[C@@H]1CCN1)c1ccc(Cl)cc1]

The title compound, MS (ISP): 239.3 ([M+H]+·) was obtained in comparable yield analogous to the procedure described for Example 12 using 4-chloroaniline instead of 4-chloro-3-methoxyaniline and (S)-2-formyl-azetidine-1-carboxylic acid tert.butyl ester instead of N-(tert-butoxycarbonyl)-L-prolinal in step a).

Example 23

(S)-1-Azetidin-2-ylmethyl-benzyl-(4-chloro-phenyl)-amine

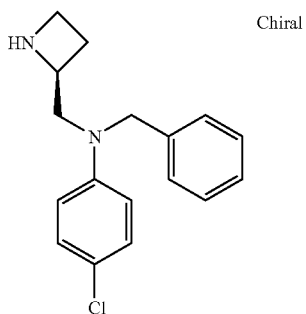 [SMILES: Clc1ccc(N(Cc2ccccc2)C[C@@H]2CCN2)cc1]

The title compound, MS (ISP): 287.3 ([M+H]+·) was obtained in comparable yield analogous to the procedure described for Example 12 using 4-dichloroaniline instead of 4-chloro-3-methoxyaniline and (S)-2-formyl-azetidine-1-carboxylic acid tert.butyl ester instead of N-(tert-butoxycarbonyl)-L-prolinal in step a) and benzaldehyd dimethylacetal instead of 2-methoxypropene in step b).

The invention claimed is:

1. A compound of formula IB

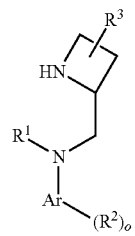

wherein
$R^1$ is hydrogen, lower alkyl or benzyl which is optionally substituted by halogen or lower alkoxy;
$R^2$ is hydrogen, halogen or OR, wherein R is lower alkyl, aryl or lower alkyl substituted by halogen;
$R^3$ is hydrogen or fluorine;
Ar is phenyl; and
o is 0, 1 or 2;
or a pharmaceutically acceptable salt thereof.

2. The compound of claim 1, selected from the group consisting of
(S)-1-azetidin-2-ylmethyl-(4-chloro-phenyl)-ethyl-amine,
(S)-1-azetidin-2-ylmethyl-ethyl-phenyl-amine,
(S)-1-azetidin-2-ylmethyl-ethyl-(3-methoxy-phenyl)-amine,
(S)-1-azetidin-2-ylmethyl-(3-bromo-phenyl)-ethyl-amine,
(S)-1-azetidin-2-ylmethyl-(4-chloro-phenyl)-methyl-amine,
(S)-1-azetidin-2-ylmethyl-(4-chloro-phenyl)-isopropyl-amine, and
(S)-1-azetidin-2-ylmethyl-benzyl-(4-chloro-phenyl)-amine.

3. A pharmaceutical composition comprising a compound of formula IB

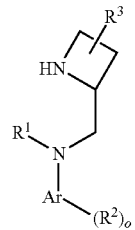

wherein
$R^1$ is hydrogen, lower alkyl or benzyl which is optionally substituted by halogen or lower alkoxy;
$R^2$ is hydrogen, halogen or OR, wherein R is lower alkyl, aryl or lower alkyl substituted by halogen;
$R^3$ is hydrogen or fluorine;
Ar is phenyl; and
o is 0, 1 or 2 and a pharmaceutically acceptable carrier.

4. The composition of claim 3, wherein the compound of formula IB is selected from the group consisting of
(S)-1-azetidin-2-ylmethyl-(4-chloro-phenyl)-ethyl-amine,
(S)-1-azetidin-2-ylmethyl-ethyl-phenyl-amine, (S)-1-azetidin-2-ylmethyl-ethyl-(3-methoxy-phenyl)-amine,
(S)-1-azetidin-2-ylmethyl-(3-bromo-phenyl)-ethyl-amine,
(S)-1-azetidin-2-ylmethyl-(4-chloro-phenyl)-methyl-amine,
(S)-1-azetidin-2-ylmethyl-(4-chloro-phenyl)-isopropyl-amine, and
(S)-1-azetidin-2-ylmethyl-benzyl-(4-chloro-phenyl)-amine.

* * * * *